US00PP33078P2

(12) United States Plant Patent
Snijder

(10) Patent No.: US PP33,078 P2
(45) Date of Patent: May 18, 2021

(54) ***PELARGONIUM* PLANT NAMED 'PEQZ0079'**

(50) Latin Name: ***Pelargonium* interspecific**
Varietal Denomination: PEQZ0079

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/922,124

(22) Filed: Jul. 7, 2020

(51) Int. Cl.
*A01H 5/02* (2018.01)
*A01H 6/42* (2018.01)

(52) U.S. Cl.
USPC ..... Plt./327
CPC ..... *A01H 6/425* (2018.05); *A01H 5/02* (2013.01)

(58) Field of Classification Search
USPC ..... Plt./327
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0079' particularly distinguished by salmon colored inflorescences with semi-double florets, held above dark green foliage, on a vigorous upright-mounding plant.

1 Drawing Sheet

Latin name of the genus and species of the plant claimed: *Pelargonium* interspecific.

Varietal denomination: 'PEQZ0079'.

BACKGROUND OF THE NEW PLANT

The present invention comprises a new *Pelargonium*, botanically known as *Pelargonium* interspecific, and hereinafter referred to by the variety name 'PEQZ0079'.

'PEQZ0079' is a product of a planned breeding program. The new cultivar 'PEQZ0079' has salmon colored inflorescences with large semi-double florets in large umbels, held above dark green foliage, on a vigorous upright-mounding plant.

'PEQZ0079' originates from a hybridization in a controlled breeding program made in July 2015, in a greenhouse in Enkhuizen, The Netherlands. The female parent was an unpatented plant of *Pelargonium* x *hortorum* parentage identified as 'PEZ-AZ3272-07' with more scarlet-red florets and poorer branching when compared to 'PEQZ0079'.

The male parent of 'PEQZ0079' was an unpatented, proprietary plant of *Pelargonium* x interspecific parentage, identified as 'PEZ-BA5017-07' with lighter green foliage and more red colored florets when compared to 'PEQZ0079'. The resultant seed was sown in December 2015.

'PEQZ0079' was selected as one flowering plant within the progeny of the stated cross in May 2016 in a greenhouse in Enkhuizen, The Netherlands.

The first act of asexual reproduction of 'PEQZ0079' was accomplished when vegetative cuttings were propagated from the initial selection in June 2016 in a greenhouse in Enkhuizen, The Netherlands.

BRIEF SUMMARY OF INVENTION

Horticultural examination of plants grown from cuttings of the plant initiated in May 2016 in Enkhuizen, The Netherlands and continuing thereafter, has demonstrated that the combination of characteristics as herein disclosed for 'PEQZ0079' are firmly fixed and are retained through successive generations of asexual reproduction.

'PEQZ0079' has not been observed under all possible environmental conditions. The phenotype may vary significantly with variations in environment such as temperature, light intensity, and day length.

A Plant Breeder's Right for this cultivar has not been applied for. 'PEQZ0079' has not been made publicly available prior to the effective filing date of this application, notwithstanding any disclosure that may have been made less than one year prior to the effective filing date of this application by the inventor or another who obtained 'PEQZ0079' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
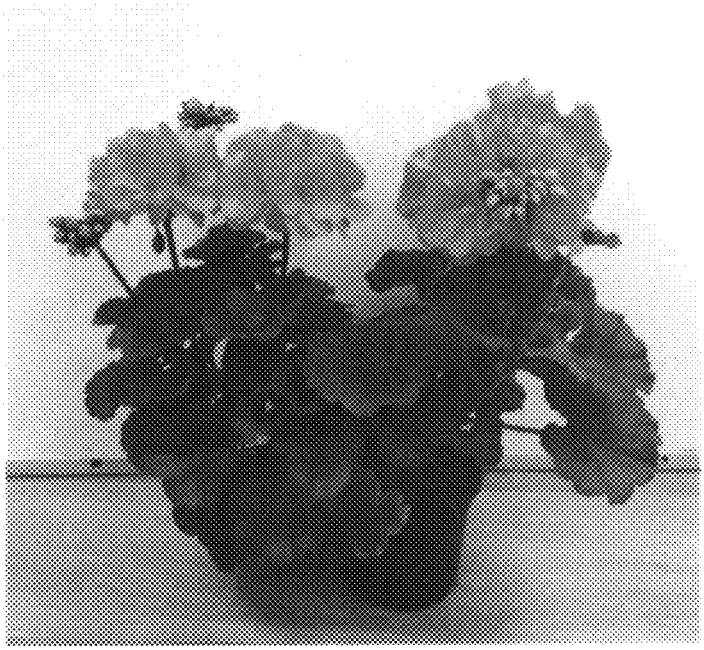
Figure 2:
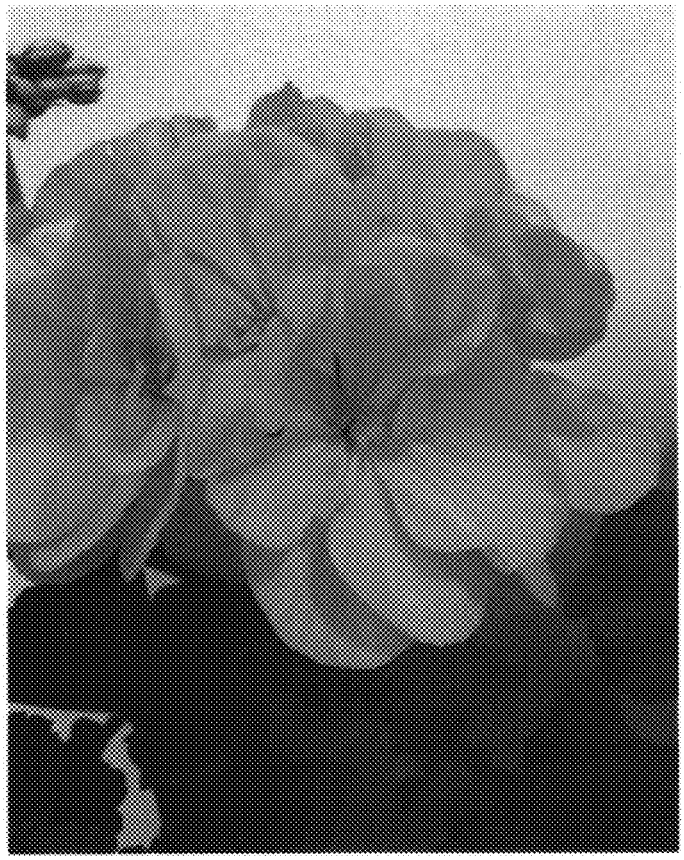

The accompanying photographic drawings show typical flower and foliage characteristics of 'PEQZ0079' with colors being as true as possible with an illustration of this type. The photographic drawings show in FIG. 1, 3 flowering plants of the new variety and in FIG. 2, a close-up of an inflorescence.

DETAILED BOTANICAL DESCRIPTION

The plant descriptions and measurements were taken in Enkhuizen, The Netherlands in early June 2020 under natural light. These plants were approximately 16 weeks old and were grown in a 12 cm pots, in a greenhouse trial. The plants shown in the photographs were about 16 weeks old growing in a 12 cm pot in a greenhouse. The photographs were taken in June 2020.

Color references are made to The Royal Horticultural Society Colour Chart (R.H.S.) 2001.

TABLE 1

DIFFERENCES BETWEEN THE NEW VARIETY 'PEQZ0079' AND A MOST SIMILAR VARIETY

| | 'PEQZ0079' | 'PEQZ0008', U.S. Plant Pat. No. 28,423 |
|---|---|---|
| Corolla form: | Single: 5 petals | Semi-double: more than 5 petals |
| Stigma color: | RHS 185A (Greyed purple) | RHS 53D (red) |

Plant:

*Form, growth and habit.*—Upright-mounding growth habit.

*Plant height.*—23-26 cm.

*Plant height (inflorescence included).*—30-34 cm.

*Plant width.*—33-38 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Variegation.*—Absent.

*Immature leaf, color upper surface.*—Closest to RHS 137A.

*Immature leaf, lower surface.*—Closest to RHS 138B.

*Mature leaf, color upper surface.*—Closest to RHS 137A.

*Mature leaf, color lower surface.*—Closest to RHS 138A.

*Length.*—6.5-8 cm.

*Width.*—7.5-10 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137A, largely indistinct.

*Color of veins, lower surface.*—RHS 144B, becoming indistinct.

*Pattern of veining.*—Palmate.

*Petiole color.*—RHS 143B, slightly mottled close to RHS 176C.

*Petiole length.*—6-7.5 cm.

*Diameter of petiole.*—0.2 cm.

*Texture.*—Pilose, hirsute, glandular hairs.

Stem:

*Quantity of branches.*—3-8.

*Color of stem.*—Close to RHS 143B.

*Length of stem.*—15-20 cm.

*Diameter.*—0.5 cm.

*Length of internodes.*—1-4 cm.

*Texture.*—Sparsely hirsute, pilose, glandular hairs.

Peduncle:

*Color of peduncle.*—RHS 187A.

*Length of peduncle.*—7-14 cm.

*Peduncle diameter.*—0.3-0.5 cm.

*Texture.*—Hirsute, glandular hairs.

Pedicel:

*Color of pedicel.*—Basal part RHS 183A.

*Length of pedicel.*—2.5-4 cm.

*Diameter of pedicel.*—0.15-0.2 cm.

*Texture.*—Sparsely pilose, glandular hairs.

Bud (just before opening):

*Color.*—RHS 52A.

*Length.*—1.2-1.4 cm.

*Width.*—0.6-0.8 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—6-12, with 3-7 immature umbels in various stages.

*Fragrance.*—None.

*Umbel diameter.*—7-13 cm.

*Umbel depth.*—7-9 cm.

Corolla:

*Form.*—Semi-double.

*Number of petals.*—7-11.

*Diameter of flower.*—4.5-5.5 cm.

*Depth of flower.*—1.5-2 cm.

*Color upper petals, upper surface.*—Closest to RHS 52A.

*Color upper petals, lower surface.*—RHS 52C, veined RHS 50A.

*Length of upper petals.*—2.2-2.5 cm.

*Width of upper petals.*—1.8-2.1 cm.

*Color lower petals, upper surface.*—RHS 52A.

*Color lower petals, lower surface.*—RHS 52A at the rim, fading to white than RHS N155A at the base, center veins RHS 52A.

*Length of lower petals.*—2.4-2.6 cm.

*Width of lower petals.*—1.8-2.2 cm, petaloids variably smaller smaller and with variable shape.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144C, base RHS 183A.

*Length of sepals.*—1-1.4 cm.

*Width of sepals.*—0.2-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—RHS 185A.

*Length.*—0.8-0.9 cm.

*Style color.*—RHS 185A.

*Style length.*—0.4-0.5 cm.

*Stigma color.*—RHS 185A.

*Ovary color*.—RHS 144A.
*Ovary length*.—0.4-0.5 cm.
*Ovary diameter*.—0.2 cm.

Androecium:

*Number of stamens*.—5-7 with 1-6 staminoids.
*Color of filaments*.—RHS N155A fading to RHS 52A at the tips.
*Length filaments*.—1.0-1.2 cm.
*Anther color*.—RHS 50C.
*Length of anthers*.—0.3 cm.
*Color of pollen*.—RHS N169B.
*Pollen amount*.—Scarce.
*Fertility/seed set*.—Has not been determined to date.
*Disease/pest resistance*.—Has not been determined to date.

What is claimed is:

1. A new and distinct variety of *Pelargonium* plant named 'PEQZ0079' substantially as illustrated and described herein.

* * * * *